US012797530B2

(12) United States Patent
Pittinger et al.

(10) Patent No.: US 12,797,530 B2
(45) Date of Patent: Nov. 17, 2026

(54) METHODS AND SYSTEMS FOR DETERMINING SUBJECT SPECIFIC AMOUNTS FOR COLLECTION

(71) Applicant: Terumo BCT, Inc., Lakewood, CO (US)

(72) Inventors: John Pittinger, Evergreen, CO (US); Thomas J. Felt, Boulder, CO (US)

(73) Assignee: Terumo BCT, Inc., Lakewood, CO (US)

(*) Notice: Subject to any disclaimer, the term of this patent is extended or adjusted under 35 U.S.C. 154(b) by 272 days.

(21) Appl. No.: 18/644,259

(22) Filed: Apr. 24, 2024

(65) Prior Publication Data

US 2024/0358906 A1 Oct. 31, 2024

Related U.S. Application Data

(60) Provisional application No. 63/462,636, filed on Apr. 28, 2023.

(51) Int. Cl.
*A61M 1/34* (2006.01)

(52) U.S. Cl.
CPC .................................. *A61M 1/3496* (2013.01)

(58) Field of Classification Search
CPC .............. A61M 1/3496; A61M 1/3696; A61M 2202/0415; A61M 2205/6009; A61M 2205/6072; A61M 2230/207
See application file for complete search history.

(56) References Cited

U.S. PATENT DOCUMENTS

| | | | | |
|---|---|---|---|---|
| RE45,315 | E | 12/2014 | Gilcher et al. | |
| 11,090,425 | B2 | 8/2021 | Felt et al. | |
| 2002/0033370 | A1 | 3/2002 | Bainbridge et al. | |
| 2012/0265099 | A1 | 10/2012 | Goodnow, II et al. | |
| 2018/0344921 | A1* | 12/2018 | Ragusa .................... | A61M 1/38 |
| 2020/0147289 | A1* | 5/2020 | Patel .................... | A61M 1/3496 |
| 2022/0168486 | A1 | 6/2022 | Patel et al. | |

(Continued)

FOREIGN PATENT DOCUMENTS

WO WO-2022086623 A1 * 4/2022 .......... A61M 1/3496

OTHER PUBLICATIONS

Written Opinion for corresponding International Patent Application No. PCT/US2024/026191 dated Aug. 8, 2024 (6 Pages).

(Continued)

*Primary Examiner* — Susan S Su
*Assistant Examiner* — Erin A Kim
(74) *Attorney, Agent, or Firm* — Harness, Dickey & Pierce, P.L.C.

(57) ABSTRACT

A method for collection blood component using a medical system includes receiving, by the medical system, data associated with an individual subject, the data associated with the individual subject including a subject's initial hematocrit; identifying, by the medical system, a subject-specific pure component amount to be collected by the medical system, the subject-specific pure component amount to be collected by the medical system determined using the subject hematocrit, a total blood volume for the subject, and a targeted change in hematocrit; and performing, using the medical system, a component donation process to collect the identified subject-specific pure component amount to be collected.

16 Claims, 13 Drawing Sheets

(56) References Cited

U.S. PATENT DOCUMENTS

| | | | |
|---|---|---|---|
| 2023/0001059 | A1 | 1/2023 | Ragusa |
| 2023/0285042 | A1 | 9/2023 | Oram et al. |
| 2023/0285232 | A1 | 9/2023 | Hillam et al. |
| 2023/0285233 | A1 | 9/2023 | Ladtkow et al. |
| 2023/0285642 | A1 | 9/2023 | Ladtkow et al. |
| 2023/0285644 | A1 | 9/2023 | Pittinger et al. |
| 2023/0285650 | A1 | 9/2023 | Ladtkow et al. |
| 2023/0285651 | A1 | 9/2023 | Pittinger et al. |
| 2023/0285652 | A1 | 9/2023 | St. George et al. |
| 2023/0285653 | A1 | 9/2023 | Pittinger et al. |
| 2023/0285654 | A1 | 9/2023 | Ladtkow et al. |
| 2023/0285655 | A1 | 9/2023 | Hake et al. |
| 2023/0285656 | A1 | 9/2023 | Hake et al. |
| 2023/0289173 | A1 | 9/2023 | St. George et al. |
| 2023/0310725 | A1 | 10/2023 | Hillam et al. |
| 2023/0310728 | A1 | 10/2023 | Polodna et al. |

OTHER PUBLICATIONS

International Search Report for corresponding International Patent Application No. PCT/US2024/026191 dated Aug. 8, 2024 (2 Pages).

* cited by examiner

METHODS AND SYSTEMS FOR DETERMINING SUBJECT SPECIFIC AMOUNTS FOR COLLECTION

CROSS-REFERENCE TO RELATED APPLICATIONS

This application claims the benefit of U.S. Provisional Application No. 63/462,636 filed Apr. 28, 2023. The entire disclosure of the above application is incorporated herein by reference.

FIELD

The present disclosure is generally directed to separating components from multi-component fluids, in particular, toward apheresis methods and systems.

BACKGROUND

This section provides background information related to the present disclosure which is not necessarily prior art.

There are two common methods for blood donation/collection. A first common method includes obtaining whole blood donation from a donor. Once the whole blood is obtained a centrifugal process may be used to separate blood components from the whole blood, for example, based on the density of different the blood component. The desired components can be manually, semi-automatically, or automatically moved to a collection container during and/or after application of the centrifugal forces. A second common method may be referred to as an apheresis collection, which requires a specialized machine. For example, the apheresis method may extract whole blood from a donor while the donor is connected to the specialized apheresis machine. The whole blood may then be centrifuged to collect only the desired blood component(s) (e.g., plasma, platelets) returning all other blood components to the donor during the same donation connection or cycle. The donor is connected to the apheresis machine during the separation and collection of the blood component. Safe, acceptable collection volumes for separation collection can be determined in response to certain features individual to the donor, including, for example, height, weight, hematocrit, and/or hemoglobin.

SUMMARY

This section provides a general summary of the disclosure and is not a comprehensive disclosure of its full scope or all of its features.

The present disclosure provides a method for collection of a blood component using a medical system.

In at least one example embodiment, the method may include receiving, by the medical system, data associated with an individual subject, the data associated with the individual subject including a subject's initial hematocrit; identifying, by the medical system, a subject-specific pure component amount to be collected by the medical system, the subject-specific pure component amount to be collected by the medical system determined using the subject's initial hematocrit, an initial total blood volume for the subject, and a targeted change in hematocrit; and performing, using the medical system, a component donation process to collect the identified subject-specific pure component amount to be collected.

In at least one example embodiment, the receiving of the data associated with the individual subject may include scanning, with a scanner, an image.

In at least one example embodiment, the scanner may be disposed on the medical system.

In at least one example embodiment, the image may include a one-dimensional barcode, a two-dimensional barcode, or a combination of a one-dimensional barcode and a two-dimensional barcode.

In at least one example embodiment, the method may further include determining, by the medical system, using the received data associated with an individual subject, an identification of the subject; and adjusting, by the medical systems, one or more parameters of the component donation process.

In at least one example embodiment, the method may further include receiving, by the medical system, data associated with a blood component collection set; and adjusting, by the medical system, one or more parameters of the component donation process.

In at least one example embodiment, the method may further include receiving, by the medical system, data associated with a component collection bottle; and adjusting, by the medical system, one or more parameters of the component donation process.

In at least one example embodiment, the data associated with the individual subject may further include the total blood volume.

In at least one example embodiment, the method may further include determining, by the medical system, using the received data associated with an individual subject, the total blood volume for the subject.

In at least one example embodiment, the method may further include determining by the medical system, using the received data associated with an individual subject, the body mass index of the subject.

In at least one example embodiment, the targeted change in hematocrit may be a preselected constant ranging from about 1% to about 15%.

In at least one example embodiment, the targeted change in hematocrit may be selected based on the subject's initial hematocrit and an acceptable post-hematocrit level.

In at least one example embodiment, a difference between the subject's initial hematocrit and the acceptable post-hematocrit level may range from about 1% to about 15%.

In at least one example embodiment, the targeted change in hematocrit may be about 8%.

In at least one example embodiment, the subject-specific pure component amount includes plasma only and the subject-specific pure component amount to be collected by the medical system may be determined, by the medical system, in accordance with the following relationship:

$$\text{pure plasma} = TBV_i - \frac{TBV_i \times hct_i}{hct_i + \text{Targeted Change in Hematocrit}}$$

where $TBV_i$ is the initial total blood volume for the subject and the $hct_i$ is the subject's initial hematocrit.

In at least one example embodiment, the method may further include after receiving the data associated with the individual subject, confirming receipt of the same using a feedback system.

In at least one example embodiment, the feedback system may include a speaker, a graphical user interface, or a speaker in combination with a graphical user interface.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations and are not intended to limit the scope of the present disclosure.

Corresponding reference numerals indicate corresponding parts throughout the several views of the drawings.

DETAILED DESCRIPTION

Figure 1:
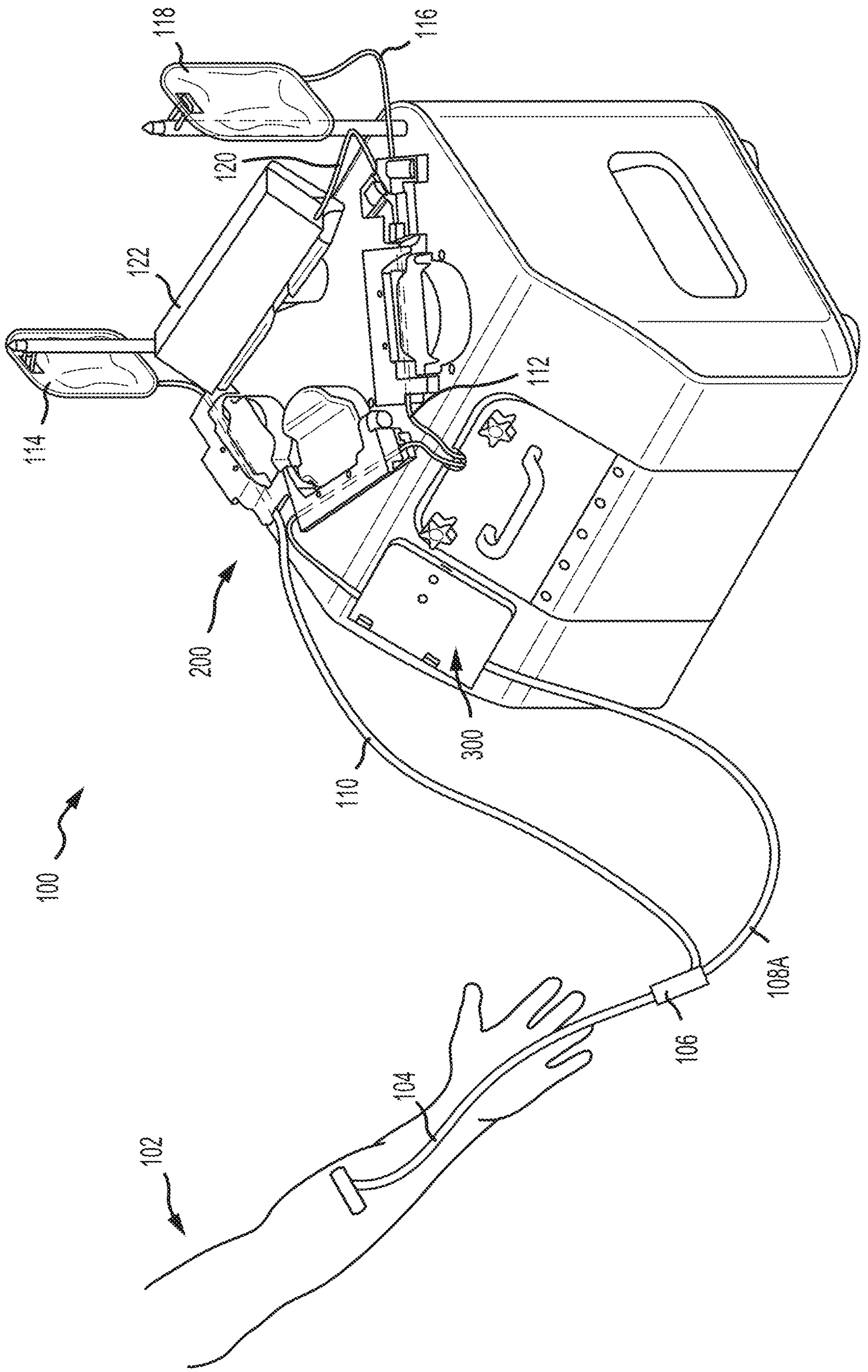
FIG. 1 is a perspective view of an operating environment of an example apheresis system in accordance with at least one example embodiment.

Example embodiments will now be described more fully with reference to the accompanying drawings.

Example embodiments are provided so that this disclosure will be thorough and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having" are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected, or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers, and/or sections, these elements, components, regions, layers, and/or sections should not be limited by these terms. These terms may be only used to distinguish one element, component, region, layer or section from another region, layer, or section. Terms such as "first," "second," and other numerical terms when used herein do not imply a sequence or order unless clearly indicated by the context. Thus, a first element, component, region, layer, or section discussed below could be termed a second element, component, region, layer, or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

Various components are referred to herein as "operably associated." As used herein, "operably associated" refers to components that are linked together in operable fashion and encompasses embodiments in which components are linked directly, as well as embodiments in which additional components are placed between the linked components. "Operably associated" components can be "fluidly associated." "Fluidly associated" refers to components that are linked together such that fluid can be transported between them. "Fluidly associated" encompasses embodiments in which additional components are disposed between the two fluidly associated components, as well as components that are directly connected. Fluidly associated components can include components that do not contact fluid but contact other components to manipulate the system (e.g., a peristaltic pump that pumps fluids through flexible tubing by compressing the exterior of the tube).

In this application, including the definitions below, the term "module" or the term "controller" may be replaced with the term "circuit." The term "module" may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

The term code, as used above, may include software, firmware, and/or microcode, and may refer to programs, routines, functions, classes, data structures, and/or objects. The term shared processor circuit encompasses a single processor circuit that executes some or all code from multiple modules. The term group processor circuit encompasses a processor circuit that, in combination with additional processor circuits, executes some or all code from one or more modules. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple modules. The term group memory circuit encompasses a memory circuit that, in combination with additional memories, stores some or all code from one or more modules.

The term memory circuit is a subset of the term computer-readable medium. The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory, tangible computer-readable medium are nonvolatile memory circuits (such as a flash memory circuit, an erasable programmable read-only memory circuit, or a mask read-only memory circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general-purpose computer to execute one or more particular functions embodied in computer programs. The functional blocks, flowchart components, and other elements described above serve as software specifications, which can be translated into the computer programs by the routine work of a skilled technician or programmer.

The computer programs include processor-executable instructions that are stored on at least one non-transitory, tangible computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation) (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Swift, Haskell, Go, SQL, R, Lisp, Java®, Fortran, Perl, Pascal, Curl, OCaml, Javascript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

Example embodiments will now be described more fully with reference to the accompanying drawings.

The present disclosure relates to methods of and means for collecting one or more blood components, like plasma, using a medical system. In at least one example embodiment, the medical system may include an apheresis system, like the apheresis systems described in U.S. Pat. No. 11,090,425, titled METHODS AND SYSTEMS FOR HIGH-THROUGHOUT BLOOD COMPONENT COLLECTION and issued Aug. 17, 2021; U.S. application Ser. No. 18/117,035, titled SOFT CASSETTE WITH INTEGRATED FEATURES and filed Mar. 3, 2023; U.S. application Ser. No. 18/116,919, titled BLOOD COMPONENT COLLECTION BLADDER and filed Mar. 3, 2023; U.S. application Ser. No. 18/117,077, titled INTEGRATED CODE SCANNING SYSTEM AND APHERESIS DATA CONTROL METHOD and filed Mar. 3, 2023; U.S. application Ser. No. 18/117,044, titled METHODS AND SYSTEMS FOR THE CALIBRATION, MAINTENANCE, AND SERVICE OF APHERESIS SYSTEMS and filed Mar. 3, 2023; U.S. application Ser. No. 18/116,902, titled MOVING BLOOD COMPONENT COLLECTION LOOP HOLDER and filed Mar. 3, 2023; U.S. application Ser. No. 18/116,958, titled BOTTLE TRAY WITH MAGNETIC COUPLING AND LOAD CELL OVERLOAD PROTECTION and filed Mar. 3, 2023; U.S. application Ser. No. 18/116,988, titled COMMUNICATIONS AND OPERATION CONTROL OF APHERESIS SYSTEMS and filed Mar. 3, 2023; U.S. application Ser. No.

18/117,006, titled METHODS AND INTERFACES FOR PROVIDING DONATION PROCESS FEEDBACK and filed Mar. 3, 2023; U.S. App. No. 18,117,007, titled MODULAR SERVICEABILITY SLEDS AND INTERCONNECTIONS and filed Mar. 3, 2023; U.S. application Ser. No. 18/116,908, titled COLLECTION BOTTLE WITH INTEGRATED CAP, HANDLE, AND SHIELD FEATURES and filed Mar. 3, 2023; U.S. application Ser. No. 18/116,992, titled METHODS FOR PROVIDING AUTOMATIC FLOW ADJUSTMENTS and filed Mar. 3, 2023; U.S. application Ser. No. 18/116,999, titled APHERESIS SYSTEM SAFETY FEATURES and filed Mar. 3, 2023; U.S. application Ser. No. 18/117,029, titled AUTOMATIC OPERATIONAL CONTROL BASED ON DETECTED ENVIRONMENTAL STATE and filed Mar. 3, 2023; U.S. application Ser. No. 18/116,954, titled FLEXURE-BASED TUBING STATE SENSOR and filed Mar. 3, 2023; U.S. application Ser. No. 18/117,035, titled SOFT CASSETTE WITH INTEGRATED FEATURES and filed Mar. 3, 2023; and U.S. application Ser. No. 18/117,073, titled BLOOD COMPONENT COLLECTION SET WITH INTEGRATED SAFETY FEATURES and filed Mar. 3, 2023, the entire disclosures of which are hereby incorporated by references.

Apheresis systems generally include one or more connections configured to move whole blood and/or blood components to and from a blood component separation device housed within the apheresis system, where the blood component separation device is a centrifuge. For example, FIG. 1 is a perspective view of an operating environment 100 of an apheresis system 200 in accordance with at least one example embodiment of the present disclosure. The operating environment 100 may include an apheresis system 200, a subject or donor or source 102, and one or more connections (e.g., donor feed tubing 104, cassette inlet tubing 108A, anticoagulant (AC) tubing 110, etc.) running from the donor 102 to the apheresis system 200 and/or vice versa. The donor feed tubing 104 may be fluidly connected with at least one blood vessel, for example, a vein, of the donor 102 via venipuncture. For example, a cannula connected to an end of the donor feed tubing 104 may be inserted through the skin of the donor 102 and into a target site, or vein. This connection may provide an intravenous path for blood to flow from the donor 102 to the apheresis system 200 and/or for blood components to flow back to the donor 102. The whole blood supplied from the donor 102 may flow along the donor feed tubing 104 through a tubing connector 106 and along the cassette inlet tubing 108A into a soft cassette assembly 300. The soft cassette assembly 300 may include one or more fluid control paths and valves for selectively controlling the flow of blood to and/or from the donor 102. The apheresis system 200 may include an anticoagulant supply contained in an anticoagulant bag 114. The anticoagulant may be pumped at least through the anticoagulant tubing 110 and the tubing connector 106 preventing the coagulation of blood in the apheresis system 200.

Figure 2:
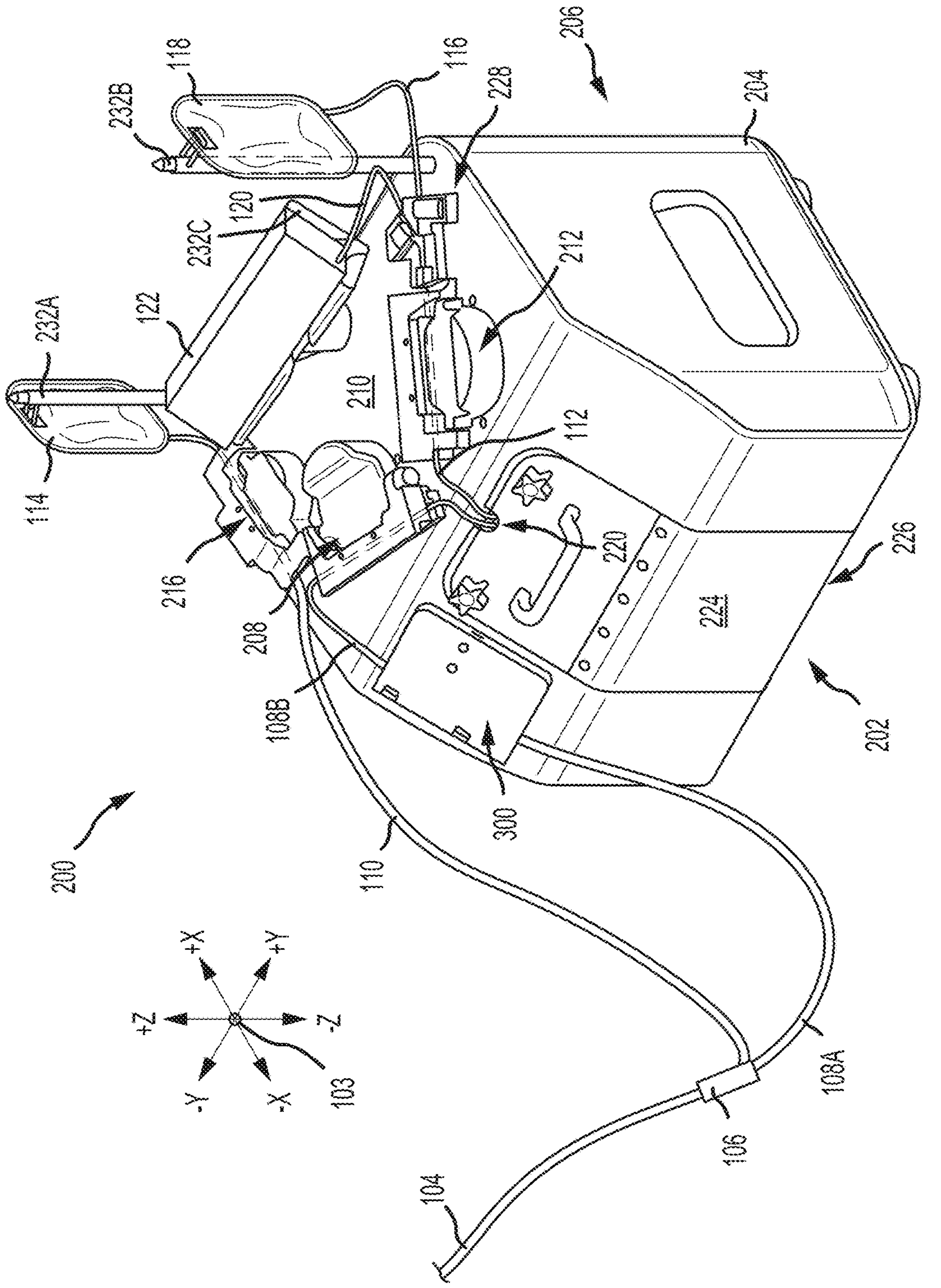
FIG. 2 is a perspective view of the example apheresis system illustrated in FIG. 1, where the access door is in a closed position in accordance with at least one example embodiment.

FIG. 2 is a perspective view of the apheresis system 200 described in FIG. 1. The apheresis system 200 may provide for a continuous whole blood separation process. In at least one example embodiment, the whole blood may be withdrawn from a donor 102 and substantially continuously provided to a blood component separation device of the apheresis system 200 where the blood may be separated into various components and at least one of these blood components may be collected from the apheresis system 200. In at least one example embodiment, one or more of the separated blood components may be either collected, for subsequent use, or returned to the donor 102. The blood may be withdrawn from the donor 102 and directed into a centrifuge of the apheresis system 200 through an opening 220 in an access panel 224 of the apheresis system 200. In at least one example embodiment, the tubing the donor feed tubing 104, the cassette inlet tubing 108A, inlet tubing 108B (also referred to herein as loop inlet tubing 108B), exit tubing 112 (also referred to herein as loop exit tubing 112), the saline tubing 116, and the plasma tubing 120, used in the extracorporeal tubing circuit may together define a closed, sterile, and disposable system, or blood component collection set, which may be further described hereinafter.

Operation of the various pumps, valves, and blood component separation device (e.g., centrifuge), may be controlled by one or more processors included in the apheresis system 200, and may advantageously comprise a plurality of embedded computer processors that are part of a computer system. The computer system may also include components that allow a user to interface with the computer system, including for example, memory and storage devices (RAM, ROM (e.g., CD-ROM, DVD), magnetic drives, optical drives, flash memory, etc.); communication/networking devices (e.g., wired such as modems/network cards, or wireless such as Wi-Fi); input devices such as keyboard(s), touch screen(s), camera(s), and/or microphone(s); and output device(s) such as display(s), and audio system(s), etc. Although not illustrated, it should be appreciated, that in at least one example embodiment, to assist the operator of the apheresis system 200 with various aspects of its operation, the blood component separation device (e.g., centrifuge), may include a graphical user interface with a display that includes an interactive touch screen.

The apheresis system 200 may include a housing 204 and/or structural frame, a cover 210, an access panel 224 disposed at a front 202 and/or rear 206 of the apheresis system 200, and one or more supports 232A-232C including hooks, rests, cradles, arms, protrusions, plates, and/or other support features for holding, cradling, and/or otherwise supporting a container or the anticoagulant bag 114, the saline bag 118, or the plasma collection bottle 122. The housing 204 may include a machine frame (e.g., made of welded, bolted, and/or connected structural elements; extruded material; and/or beams) to which one or more panels, such as the cover 210, doors, subassemblies, and/or components are attached. In at least one example embodiment, at least one panel of the apheresis system 200 may include a mounting surface for the soft cassette assembly 300, one or more pumps such as a draw pump 208, a return pump 212, an anticoagulant pump 216, and/or a fluid valve control system 228 (e.g., plasma and saline valve control).

The access panel 224 may include one or more handles, locks, and a pivoting or hinged axis 226 (e.g., a door hinge, piano hinge, continuous hinge, cleanroom hinge, etc.). The access panel 224 may be selectively opened to provide access to an interior of the apheresis system 200, and more specifically, to a blood separation assembly, (e.g., centrifuge assembly). For example, the access panel 224 may provide access to load and/or unload the centrifuge with one or more components in the blood component collection set. In at least one example embodiment, the inside of the apheresis system 200 may be separated into at least a centrifuge portion and a controls portion. For example, the centrifuge portion may include a cavity configured to receive the centrifuge, rotation motor, and associated hardware. This area may be physically separated from the controls portion via one or more walls of the cavity. In at least one example embodiment, access to the controls portion (e.g., configured to house or otherwise contain the motor controller, CPU or processor(s), electronics, and/or wiring) may be provided via a securely fastened panel of the housing 204 and/or panel separate from the access panel 224.

In at least one example embodiment, the apheresis system 200 may include a number of pumps, such as the draw pump 208, the return pump 212, and/or the anticoagulant pump 216, which can be configured to control the flow of fluid (e.g., blood and/or blood components, anticoagulant, and/or saline) through the apheresis system 200. As shown in FIG. 2, in at least one example embodiment, the draw pump 208, the return pump 212, and/or the AC pump 216 may be disposed at least partially on a top portion of the cover 210 of the apheresis system 200. In at least one example embodiment, the draw pump 208 may controls blood flow to and/or from the donor 102 into the centrifuge of the apheresis system 200. For example, the draw pump 208 may engage with a portion of the inlet tubing 108B disposed between the soft cassette assembly 300 and the centrifuge of the apheresis system 200. In at least one example embodiment, the return pump 212 may be configured to control a flow of separated blood components (e.g., plasma) from the centrifuge to a plasma collection bottle 122 and/or vice versa. Additionally, or alternatively, the return pump 212 may control a flow of saline (e.g., supplied from the saline bag 118) throughout the blood component collection set and/or apheresis system 200. In at least one example embodiment, the anticoagulant pump 216 may engage with a portion of the anticoagulant tubing 110 to selectively control the flow of anticoagulant throughout the blood component collection set of the apheresis system 200.

Figure 3:
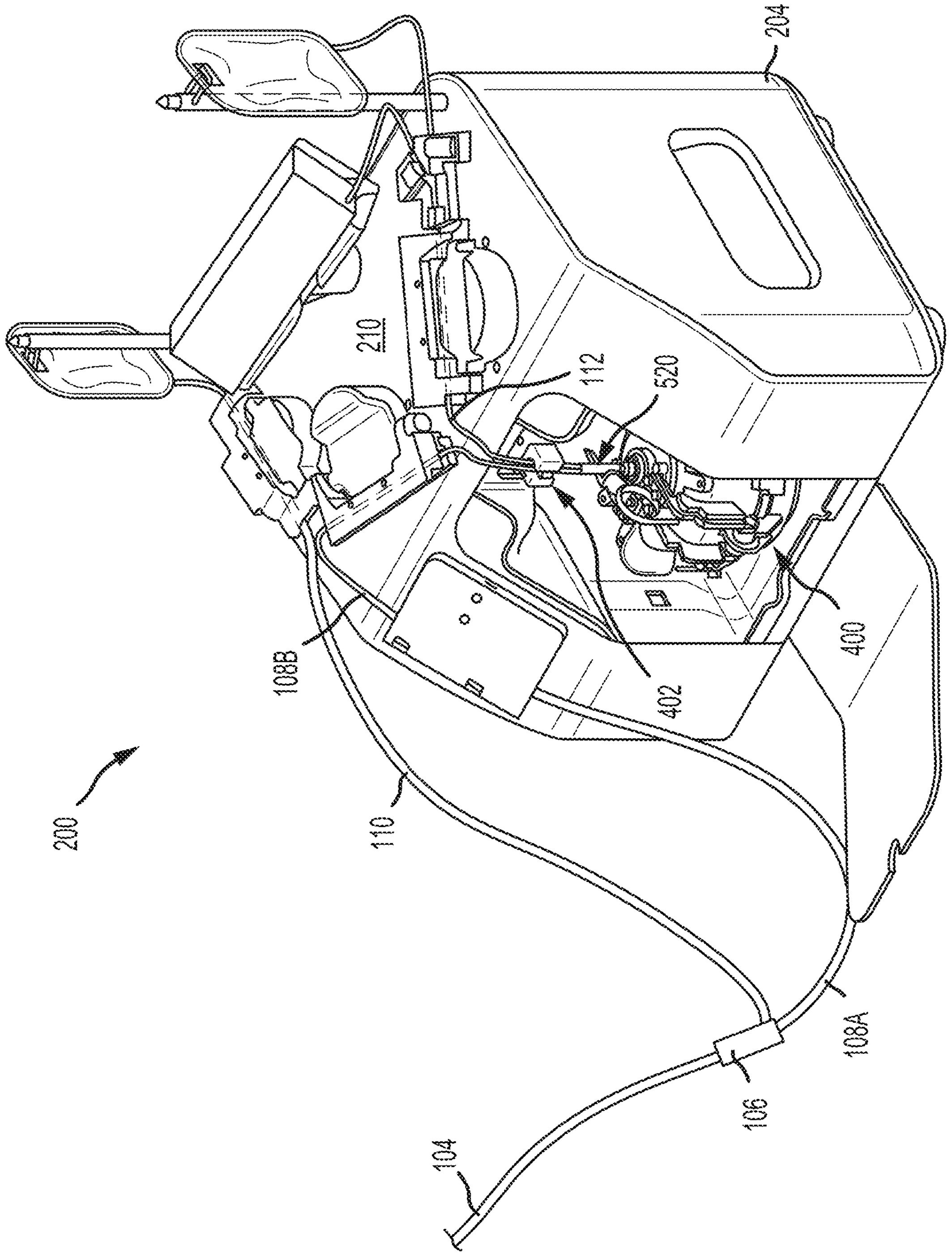
FIG. 3 is a perspective view the example apheresis system illustrated in FIGS. 1-2, where the access door is in an open position revealing a centrifuge assembly in accordance with at least one example embodiment.

FIG. 3 illustrates an example centrifuge assembly 400 for use with or in the apheresis system 200 in accordance with at least one example embodiment of the present disclosure. For example, the centrifuge assembly 400 may be disposed in an interior space of the apheresis system 200. The interior space may be at least partially enclosed with one or more elements of the housing 204 and/or centrifuge chamber. Access to the interior space and the centrifuge assembly 400 may be provided via the access panel 224 disposed at the front 202 of the apheresis system 200. For example, in FIG. 4A, the access panel 224 is shown in an open position, opened along the hinged axis 226. The hinged axis 226 may correspond to a door hinge, continuous hinge, cleanroom hinge, and/or other panel hinges.

The centrifuge assembly 400 may be operatively mounted inside the apheresis system 200 such that the assembly 400 is capable of rotating relative to the housing 204 and/or other elements of the apheresis system 200. The centrifuge assembly 400 may be loaded with one or more portions of the blood component collection set by routing tubing (e.g., the inlet tubing 108B and the exit tubing 112) into the interior space of the apheresis system 200 (e.g., via the opening 220 shown in FIG. 2), connecting a portion of a blood component collection loop 520 to the fixed loop connection 402 and inserting a blood component collection bladder into a filler 460. The fixed loop connection 402 maintains the inlet tubing 108B and the exit tubing 112 in a fixed position and may prevent twisting of the tubing 108B, 112 outside of the apheresis system 200. In at least one example embodiment, the blood component collection loop may be interconnected to the fixed loop connection 402 via one or more keyed features or positive location features.

Figure 4:
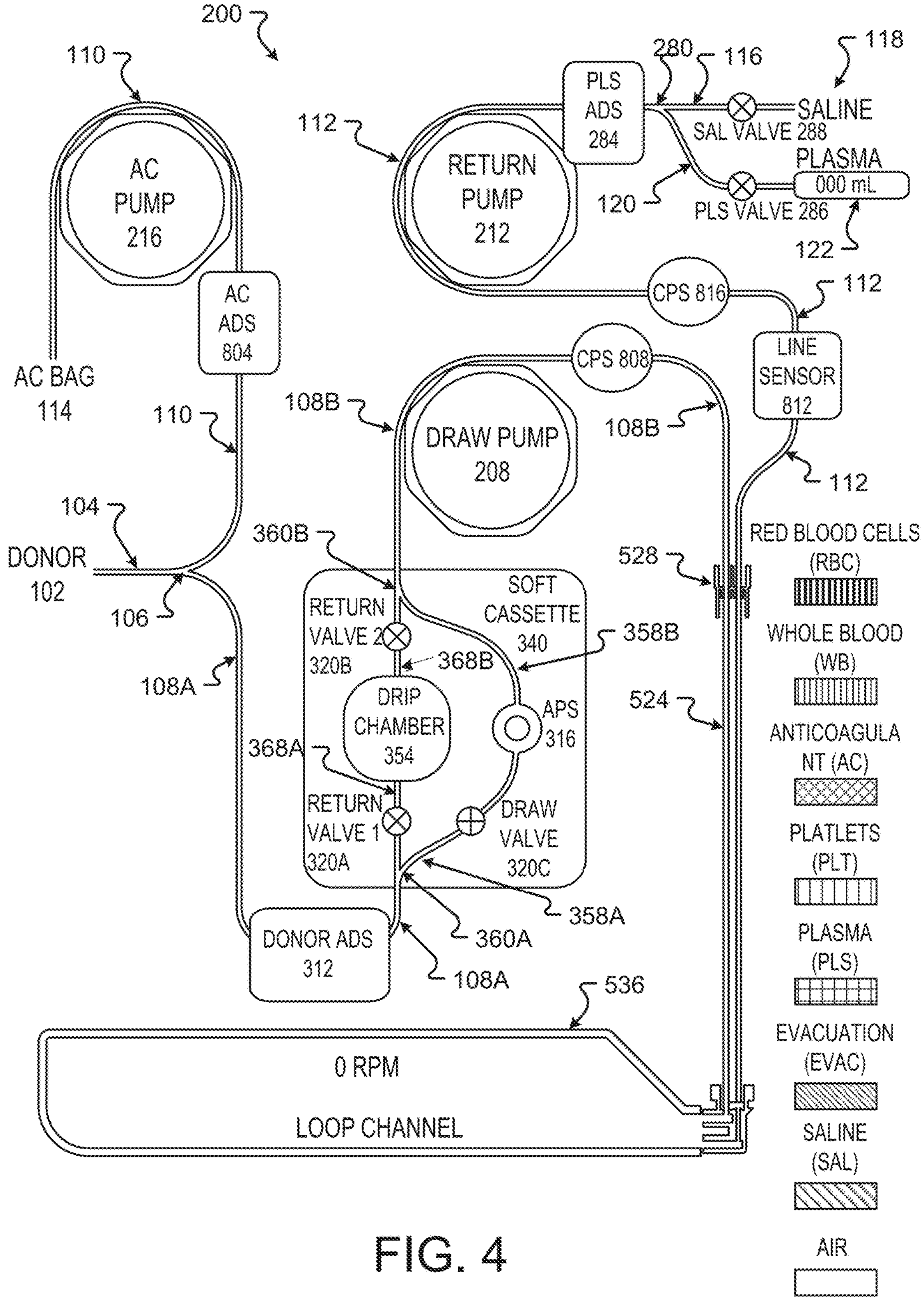
FIG. 4 is a functional diagram of an example embodiment of the example apheresis system illustrated in FIGS. 1-3 in accordance with at least one example embodiment.

FIG. 4 provides a functional diagram of the apheresis system 200 illustrated in FIGS. 1-3. FIG. 4 shows the components as previously introduced in a functional diagram to describe the operation of the system 200 for extracting plasma or other blood components from the whole blood of a donor 102 during an apheresis procedure or process. For example, as illustrated in FIG. 4, the anticoagulant pump 216 may be configured to pump fluid in the anticoagulant tubing 110 from the anticoagulant bag 114. In at least one example embodiment, the anticoagulant tubing 110 may also include an anticoagulant air detection sensor (ADS) 804 configured to detect air or fluid within the anticoagulant tubing 110. The anticoagulant tubing 110 may intersect with and be fluidly associated with the donor feed tubing 104 and also the cassette inlet tubing 108A at tubing connector 106. The tubing connector 106 may be any type of connection configured to connect the different tube 110, 104, and/or 108A.

The donor feed tubing 104 proceeds from the donor 102, where the donor 102 may be stuck with a lumen needle or other device, allowing whole blood to flow from the donor 102 into the apheresis system 200 and allowing blood components to flow back to the donor 102. The tubing 108A proceeds to the soft cassette 340. In at least one example embodiment, a donor air detection sensor (ADS) 312 can be placed on or in the tubing 108A. The donor air detection sensor may be configured to detect the presence of fluid and/or air within tubing 108A.

The soft cassette 340 may include a first cassette port 360A where the tube 108A breaks into first and second tubing sections. For example, the first cassette port 360A can function as, include, and/or be substantially proximate to a “Y” connector or section that separates the tubing 108A into the first bypass branch 358A and the first tubing section 368A. The two tubing sections and can reconnect at the second cassette port 360B, which like the first cassette port 360A, can function as, include, and/or be substantially proximate to a “Y” connector or section. In at least one example embodiment, the first tubing may be bisected by a fluid sensor 316 forming a first bypass branch 358A and a second bypass branch 358B. In at least one example embodiment, the first bypass branch 358A may include a first fluid control valve 320C. In at least one example embodiment, the second tubing may be bisected by the drip chamber 354 forming a first tubing section 368A and a second tubing section 368B. The drip chamber 354 may be configured to collect a volume of whole blood and/or high hematocrit blood (blood with a high percentage of red blood cells) depending on the operation of the system 200. In at least one example embodiment, the first tubing section 368A may include a second fluid control valve 320A, while the second tubing section 368B includes a third fluid control valve 320B. The fluid control valves 320A, 320B, 320C may be configured to isolate the different tubing portions 358A, 368A, 358B, 368B.

The inlet tubing 108B may be connected to the second cassette port 360B and may connect the soft cassette 340 to the flexible loop 524. In at least one example embodiment, the inlet tubing 108B may include a sensor 808, disposed on or in the tubing 108B before a system static loop connector 528 of the flexible loop 524. In at least one example embodiment, the inlet tubing 108B may include a pressure sensor (CPS) 808 disposed between the second cassette port 360B and the system static loop connector 528. In each instance, a draw pump 208 may be configured to pumped fluid through the tubing 108B either away from the soft cassette 340 or towards the soft cassette 340.

Two or more different tubes may be connected to the flexible loop 524 via the system static loop connector 528 and may provide fluid to, or receive fluid from, a blood component collection bladder 536. In at least one example embodiment, an exit tubing 112 may be connected to the flexible loop 524 via the system static loop connector 528. In at least one example embodiment, the exit tubing 112 may include another line sensor 812 that is disposed thereon or therein and is configured to detect fluid, air, cellular concentration, color, and/or color change in the fluid moving from the flexible loop 524. In at least one example embodiment, a second pressure sensor or fluid sensor 816 may also be disposed in or on line 112. The sensor 816 may be configured to detect one or more of the presence or absence of fluid within the exit tubing 113, pressure within the exit tubing 112, and/or other characteristics of the fluid in exit tubing 112. In each instance, the exit tubing 112 may flow into a plasma air detection sensor 284 before a saline and plasma tubing y-connector 280 separates the exit tubing 112 into saline tubing 116 and plasma tubing 120. In at least one example embodiment, a return pump 212 may engage with the exit tubing 112 to cause fluid or air to flow through the exit tubing 112 from either the flexible loop 524 or a saline bag 118 and/or a plasma collection bottle 122.

Figure 5:
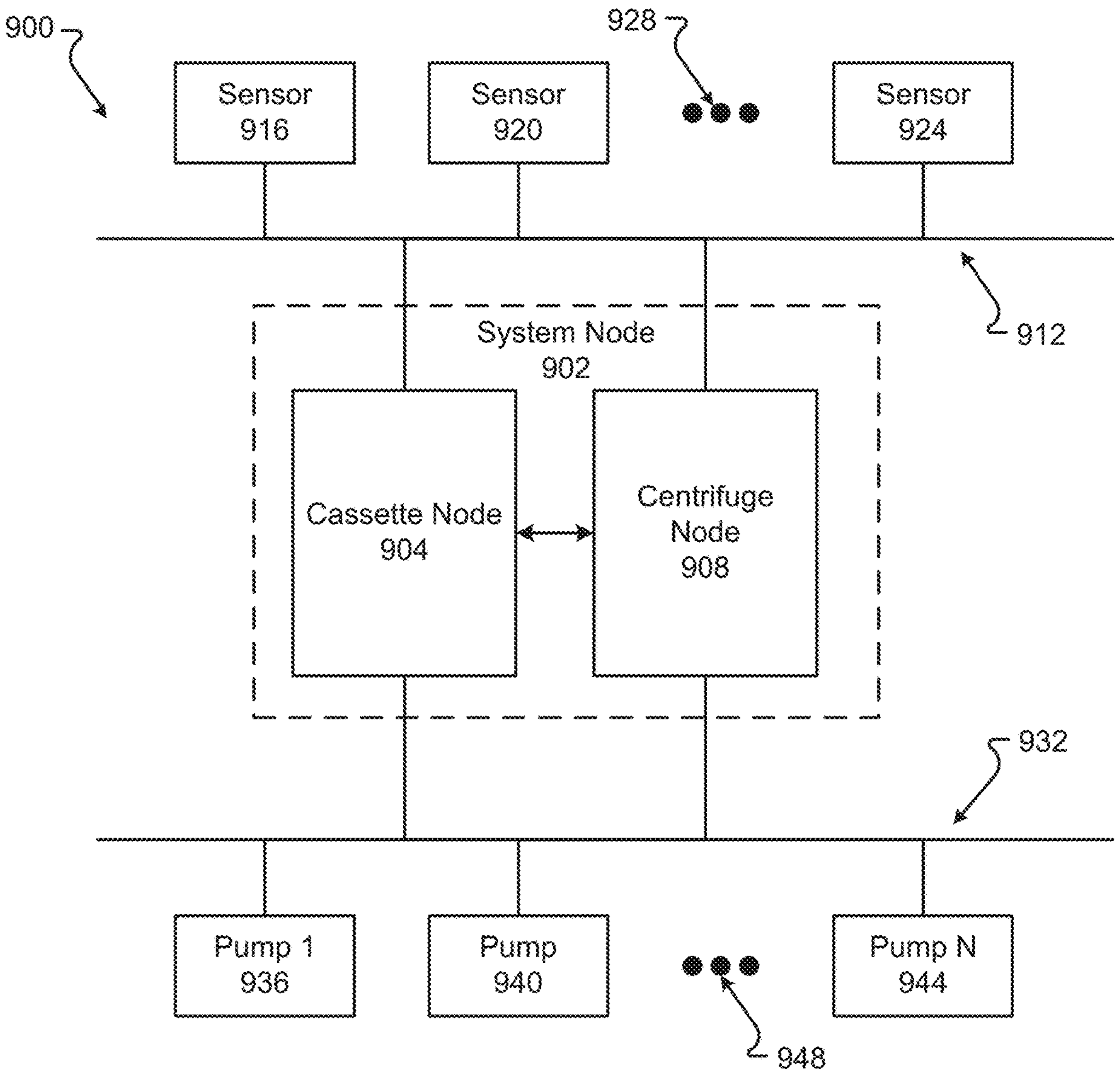
FIG. 5 is a block diagram of an example electrical system of the example apheresis system illustrated in FIGS. 1-4 in accordance with at least one example embodiment.

FIG. 5 illustrates an example electrical and control system 900 configured to control the functions of the apheresis system 200 illustrated in FIGS. 1-4. Generally, the control system 900 may include one or more nodes, which can include various hardware, firmware, and/or software configured to control and/or communicate with the mechanical, electromechanical, and electrical components of the apheresis system 200. Each node may be configured to control a different part of the apheresis system 200. For example, the control system 900 may include a cassette node 904 which may be a soft cassette assembly system may be configured to control and/or communicate with the components of a blood component collection set (and/or the associated hardware or mechanical components interfacing with blood component collection set or components thereof). The centrifuge node 908 which may be a centrifuge system may be configured to control and/or communicate with the centrifuge assembly 400 (and/or the associated hardware or mechanical components associated the with the centrifuge assembly 400 or components thereof). In at least one example embodiment, the cassette node 904 and centrifuge node 908 may be in communication with each other either wirelessly or through some other electrical or data connection. In at least one example embodiment, the cassette node 904 and centrifuge node 908 may separate portions of a single node or system 902. In at least one example embodiment, the cassette node 904 and centrifuge node 908 may have the same or different physical hardware that is used to operate and/or control different functions.

Each of the cassette node 904 and the centrifuge node 908 may be in communication with one or more sensors 916, 920, and/or 924. There may be more or fewer sensors than those shown in FIG., as represented by ellipsis 928. Each of the cassette node 904 and/or the centrifuge node 908 can communicate directly to each sensor 916-924, or in other embodiments, may communicate with the several sensors 916-924 via a bus 912. The bus 912 may communicate by any type of communication protocol, such as universal serial bus (USB), a universal asynchronous receive/transmit (UART), or other types of bus systems or parallel communication connections. The sensors 916-924 can be any type of sensor that can communicate information, for example, about light, fluid, the presence of air, color, and/or pressure. Some of the sensors 916-924 may include sensors such as the air detection sensor 312, the fluid sensor 316, the anticoagulant air detection sensor 804, the pressure sensor 808, the line sensor 812, the second pressure sensor 816, and/or the air detection sensor 284.

Figure 9:
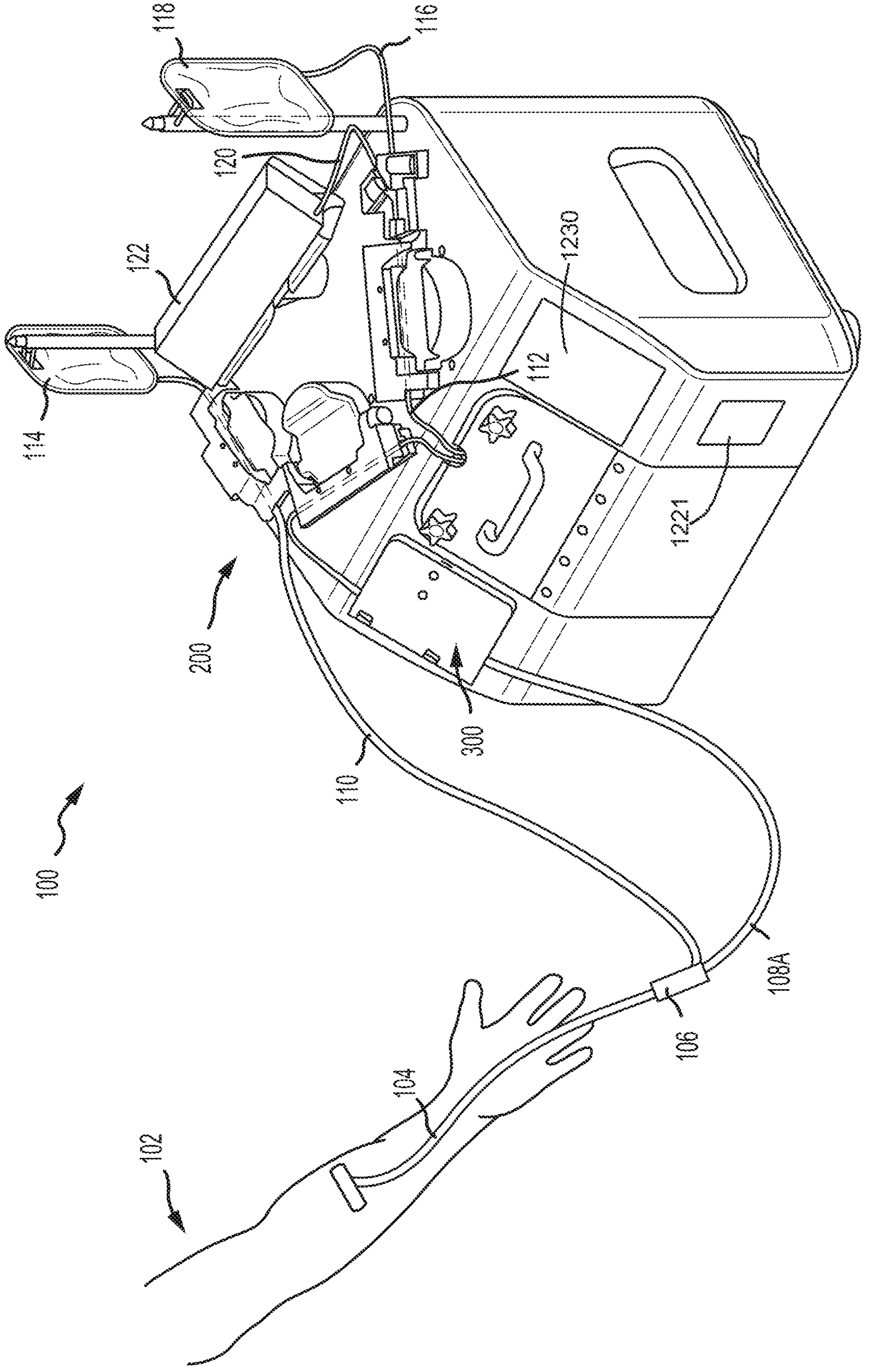
FIG. 9 is a perspective view of the example apheresis system illustrated in FIGS. 1-8 further including a scanner in accordance with at least one example embodiment.

Each of the cassette node 904 and the centrifuge node 908 may be in communication with one or more pump drives, pump motors, 936, 940, 944 (referred to collectively as "pumps"). There may be more or fewer pumps than are shown in FIG. 9, as represented by ellipsis 948. The cassette node 904 and/or the centrifuge node 908 may communicate with the pumps 936-944 through direct wired or wireless communication or through a bus 932. The bus 932 can be a control area network (CAN) bus, universal serial bus, or other type of bus architecture to communicate with the pumps 936-944. The pumps 936-944 can include, or be a part of, at least one of the draw pump 208, the return pump 212, and/or the anticoagulant pump 216.

Figure 6:
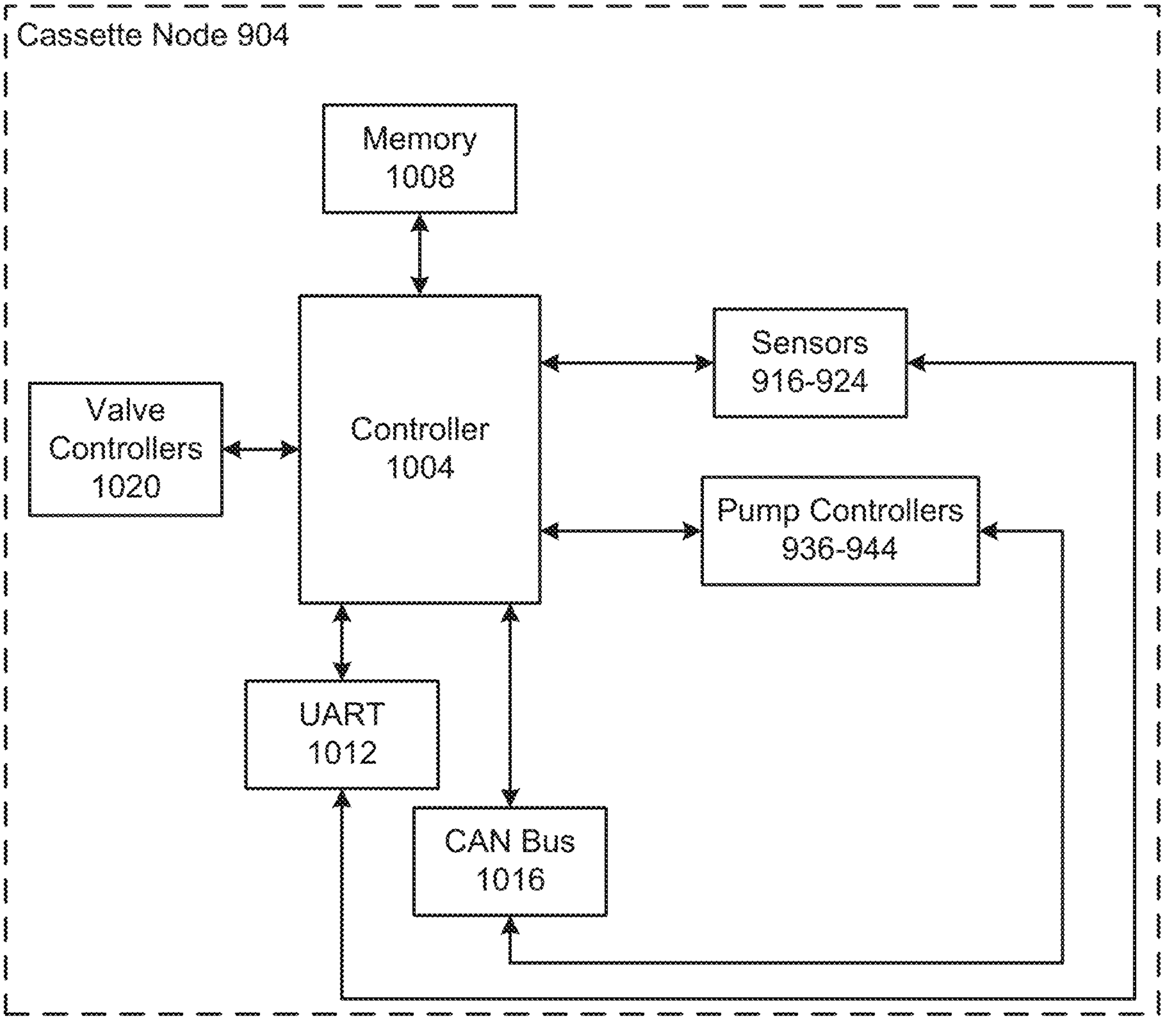
FIG. 6 is a further block diagram of the example electrical system of example apheresis system illustrated in FIGS. 1-5 in accordance with at least one example embodiment.

FIG. 6 illustrates an example cassette node 904. As illustrated, in at least one example embodiment, the cassette node 904 may include one or more of a controller 1004, a memory 1008, a valve controller 1020, a communication interface for a control area network bus 1016, a communication interface for a universal asynchronous receive/transmit 1012, and a communication interface for other types of buses. Although not illustrated, it should be recognized that the cassette node 904 can also include other hardware, firmware, and/or software.

The controller 1004, which may also be referred to as a processor, may be any type of microcontroller, microprocessor, Field Programmable Gate Array (FPGA), Application Specific Integrated Circuit (ASIC), etc. An example controller 1004 may be the NK10DN512VOK10 microcontroller, made and sold by N9P USA, Incorporated, which is a microcontroller unit with a 32-bit architecture. Other types of controllers, however, are possible. In each instance, the controller 1004 is configured to control other types of devices and/or to direct the functions of other types of devices, such as valves such as the first fluid control valve 320A, the second fluid control valve 320B, the draw fluid control valve 320C, the plasma flow control valve 286, the saline flow control valve 288, and/or the pumps 936-944. The controller 1004 may also be configured to communicate with various sensors 916-924 or other devices to receive and/or send information regarding the function of the apheresis system 200.

Other examples of the controller 1004, may include, but are not limited to, at least one of Qualcomm® Snapdragon® 800 and 801, Qualcomm® Snapdragon® 610 and 615 with 4G LTE Integration and 64-bit computing, Apple® A7 processor with 64-bit architecture, Apple® M7 motion coprocessors, Samsung® Exynos® series, the Intel® Core™ family of processors, the Intel® Xeon® family of processors, the Intel® Atom™ family of processors, the Intel Itanium® family of processors, Intel® Core® i5-4670K and i7-4770K 22 nm Haswell, Intel® Core i5-3570K 22 nm Ivy Bridge, the AMD® FX™ family of processors, AMD® FX-4300, FX-6300, and FX-8350 32 nm Vishera, AMD® Kaveri processors, ARM® Cortex™-M processors, ARM® Cortex-A and ARM926EJ-S™ processors, other industry-equivalent processors, and may perform computational functions using any known or future-developed standard, instruction set, libraries, and/or architecture.

The memory 1008 can be any type of memory including random access memory (RAM), read only memory (ROM), electrically erasable programmable ROM (EEPROM), a portable compact disc read-only memory (CD-ROM), an optical storage device, a magnetic storage device, any suitable combination of the foregoing, or other type of storage or memory device that stores and provides instructions to program and control the controller 1004. The memory 1008 may provide all types of software or firmware that programs the functions of the controller 1004.

The controller 1004 can communicate with one or more valve controllers 1020. Valves, such as such as the first fluid control valve 320A, the second fluid control valve 320B, the draw fluid control valve 320C, the plasma flow control valve 286, and/or the saline flow control valve 288, may be controlled by a valve controller 1020 and may be associated with a component of the system 200 . . . . The valve controller 1020 can provide the electrical signal, operational directive, or power to close or open any one of the valves, for example, the saline and plasma valve housing 276, the plasma flow control valve 286, the saline flow control valve 288, the first fluid control valve 320A, the second fluid control valve 320B, and/or the draw fluid control valve 320C.

The controller 1004 can also be connected to a bus 912, 932 through transceivers 1012, 1016 provided outside of the controller 1004 or integral to the controller 1004. The universal asynchronous receive/transmit transceiver 1012 may communicate with one or more of the sensors 916-924 or other devices. Likewise, the control area network bus transceiver 1016 can communicate with one or more of the pump controllers 936-944 or other devices. universal asynchronous receive/transmit transceivers 1012 and busses and control area network bus transceivers 1016 and busses are well known in the art and need not be explained further herein.

Figure 7:
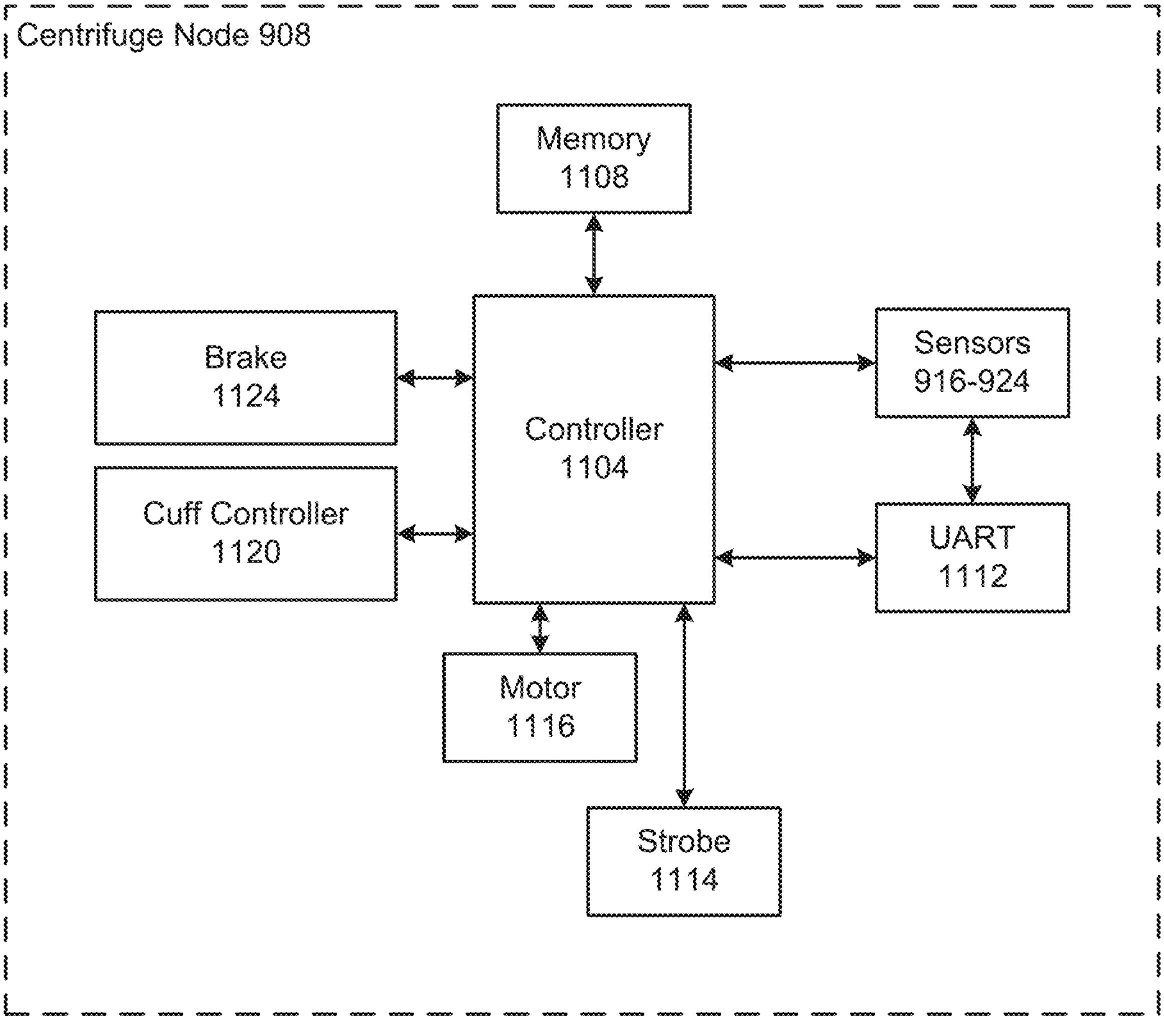
FIG. 7 is a further block diagram of the example electrical system of example apheresis system illustrated in FIGS. 1-5 in accordance with at least one example embodiment.

FIG. 7 illustrates an example centrifuge node 908. The centrifuge node can include the same or similar types of components as the cassette node 904. For example, in at least one example embodiment, as illustrated, the centrifuge node 908 may include a controller 1104 and/or a universal asynchronous receive/transmit transceiver 1112. Similar to the controller 1004, in at least one example embodiment, the controller 1104 may include any type of processor or microcontroller, including, for example, the NK10DN512VOK10 microcontroller unit with 32-bit architecture from N9P USA, Incorporated.

In at least one example embodiment, the controller 1104 may be configured to communicate with the sensors 916-924, for example, directly, through the universal asynchronous receive/transmit transceiver 1112 and/or through other busses or systems. In at least one example embodiment, the controller 1104 may be configured to communicate with a brake controller 1124. The brake controller 1124 may be configured to brake or slow and stop the centrifuge 400. In at least one example embodiment, the controller 1104 may be configured to communicate with a motor transceiver 1116. The motor transceiver 1116 may be configured to communicate with a motor power system or a motor controller that functions to spin up or rotate the centrifuge 400 and/or control the speed setting or other function of the centrifuge 400. In at least one example embodiment, the controller 1104 may be configured to communicate with a cuff controller 1120 that can change or set the pressure of a pressure cuff on a donor's 102 arm during the apheresis process. In at least one example embodiment, the controller 1104 may be configured to communicate a strobe light 1114 which can be any light that flashes at a periodicity in synchronicity with the rate of spin of the motor, such that an operator of the apheresis system 200 can see the operation of the filler 460. The controller 1104 may be configured to communicate with the strobe light 1114 so as to change the frequency of the flashing of the strobe light 1114 and/or the intensity of the strobe light 1114.

Figure 8:
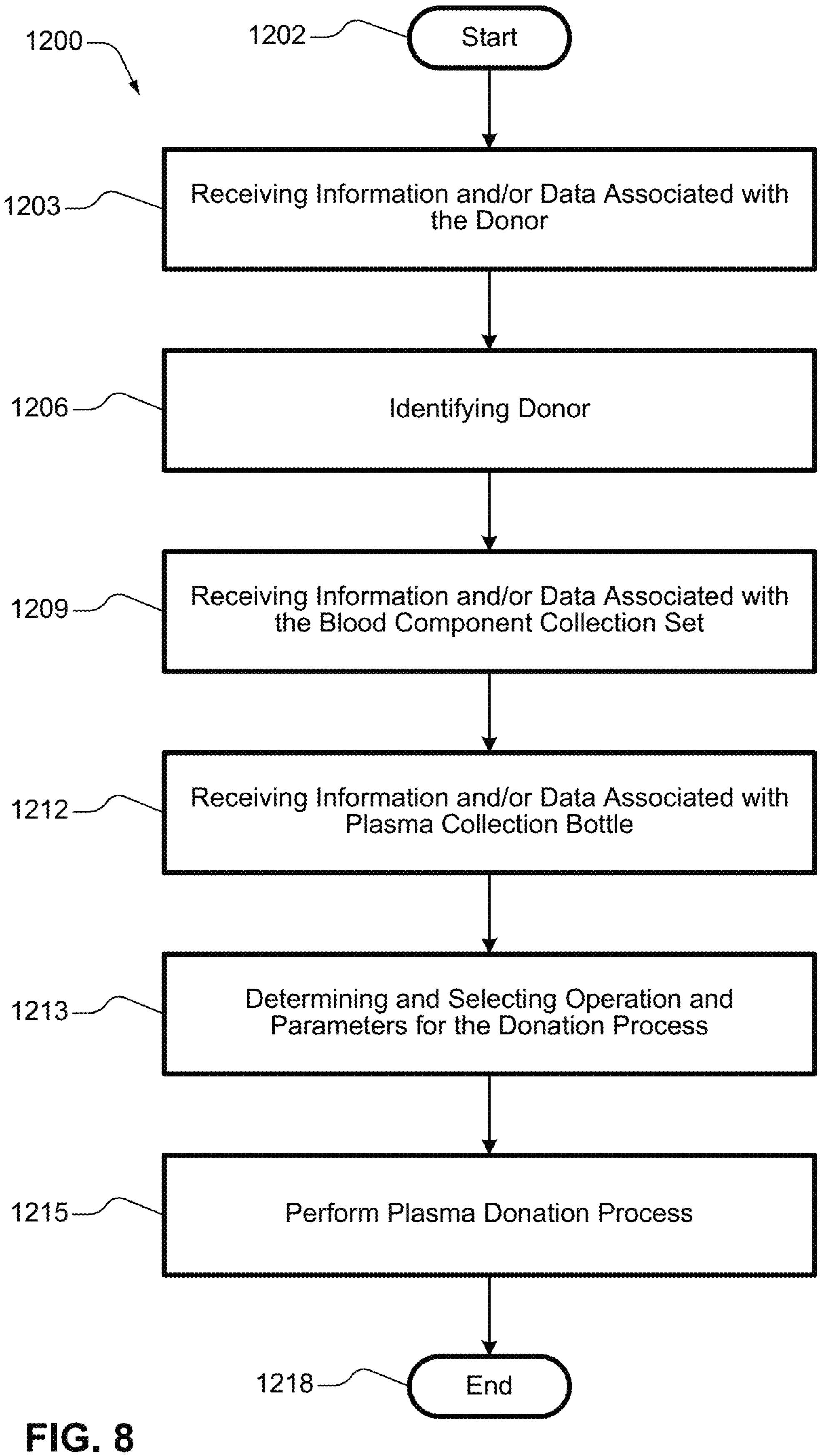
FIG. 8 is a flowchart illustrating an example method of using the apheresis system illustrated in FIGS. 1-7 in accordance with at least one example embodiment.

FIG. 8 is a flowchart illustrating an example data entry process 1200, for example, for initializing the apheresis system 200 illustrated in FIGS. 1-7. The data entry process 1200 may help to ensure that a target amount or volume of plasma (or other blood component) based on donor information is obtained. Also, in at least one example embodiment, that data entry process 1200, may allow for entry of other information, like bottle identification information and/or collection set information such that the apheresis system 200 is capable of recording an indication as to which bottle and/or collection set was used for which donor 102. The data entry process 1200 of FIG. 8 may begin at 1202 where the apheresis system 200 is powered on to await a new donor 102.

In at least one example embodiment, as illustrated in FIG. 9, the apheresis system 200 may include an integrated identification reader (e.g., radio-frequency identification (RFID) reader, barcode reader, etc.) 1221 that is configured to read a code (e.g., radio-frequency identification tag, barcode, etc.) associated with a particular donor 102 and to control and/or determine certain operation parameters of the apheresis system 200 in accordance with the information received by the identification reader. The information and/or data may include biological information, including, for example, age, weight, height, hematocrit, hemoglobin, donor history, and/or other information which may be relevant to the donation process. With renewed reference to FIG. 8, the data entry process 1200 may include receiving 1203 the donor-specific information. For example, the apheresis system 200 may be configured to scan a barcode, quick release code, or other type of image to receive donor-specific information. For example, in at least one example embodiment, the donor 102 may use an identification card, or other type of object, which may include one or more of a barcode, quick release code, and/or radio-frequency identification. The identification card, or other type of object, may be portable between donation sites, apheresis systems, and/or locations. The donor-specific information may be stored in or on the identification card, or other type of object, in the form of a nomogram, for example, in a two-dimensional barcode. In this way, a donor 102 may carry a single form of identification between donation sites and each donation site may be enabled to collect information about the donor 102, such as time since the last visit.

By scanning the identification card, or other type of object, the apheresis system 200 may receive, or be enabled to receive, information and/or data relating to the individual donor 102, for example, without requiring further input from the user via the user interface. The apheresis system 200 may be enabled to receive the information, confirm entry of the data automatically, and evaluate the information without human input. The received information may be used for faster, safer, and higher quality donor experiences. For example, the information received from the donor 102 may be used to determine whether the donor 102 qualifies for the donation procedure and to determine particular settings which may be required for the donation procedure, such as a total expected amount of plasma or other information.

In at least one example embodiment, the identification card, or other type of object, may contain information regarding the weight and/or the height and/or the hematocrit and/or the hemoglobin of the donor 102, which may be used, alone or in combination, to define an amount or volume of plasma (or other blood component) the donor 102 can provide or donate. For example, as can be appreciated, a donor 102 having a first weight may be allowed, in certain instances, to donate a first amount of plasma while a donor 102 having a heavier second weight may be allowed, in certain instances, to donate a second amount of plasma that is greater than the first amount. Additionally, or alternatively, the body mass of the donor 102 may be used to define the amount or volume of plasma (or other blood component) the donor 102 can provide or donate. Once the apheresis system 200 receives the information, the apheresis system 200 may adjust various settings and/or promote one or more steps for the nurse, practitioner, or other user or operator of the apheresis system 200 using a graphical user interface (GUI) in accordance therewith, including initiating and ceasing operations in response to a determine or predating donation volume or event.

In at least one example embodiment, the stored in, or carried by, the identification card, or other type of object, (for example, in the form of a nomogram) may be limited to information that the apheresis system 200 is allowed to collect (e.g., by privacy laws, health laws, etc.). In at least one example embodiment, donor information and/or data that is not allowed to be collected by the apheresis system 200 may be encrypted, or locked, such that the apheresis system 200 (and more specifically, the integrated identification reader 1221) is unable to read and/or obtain the noted information and/or data.

Figure 10:
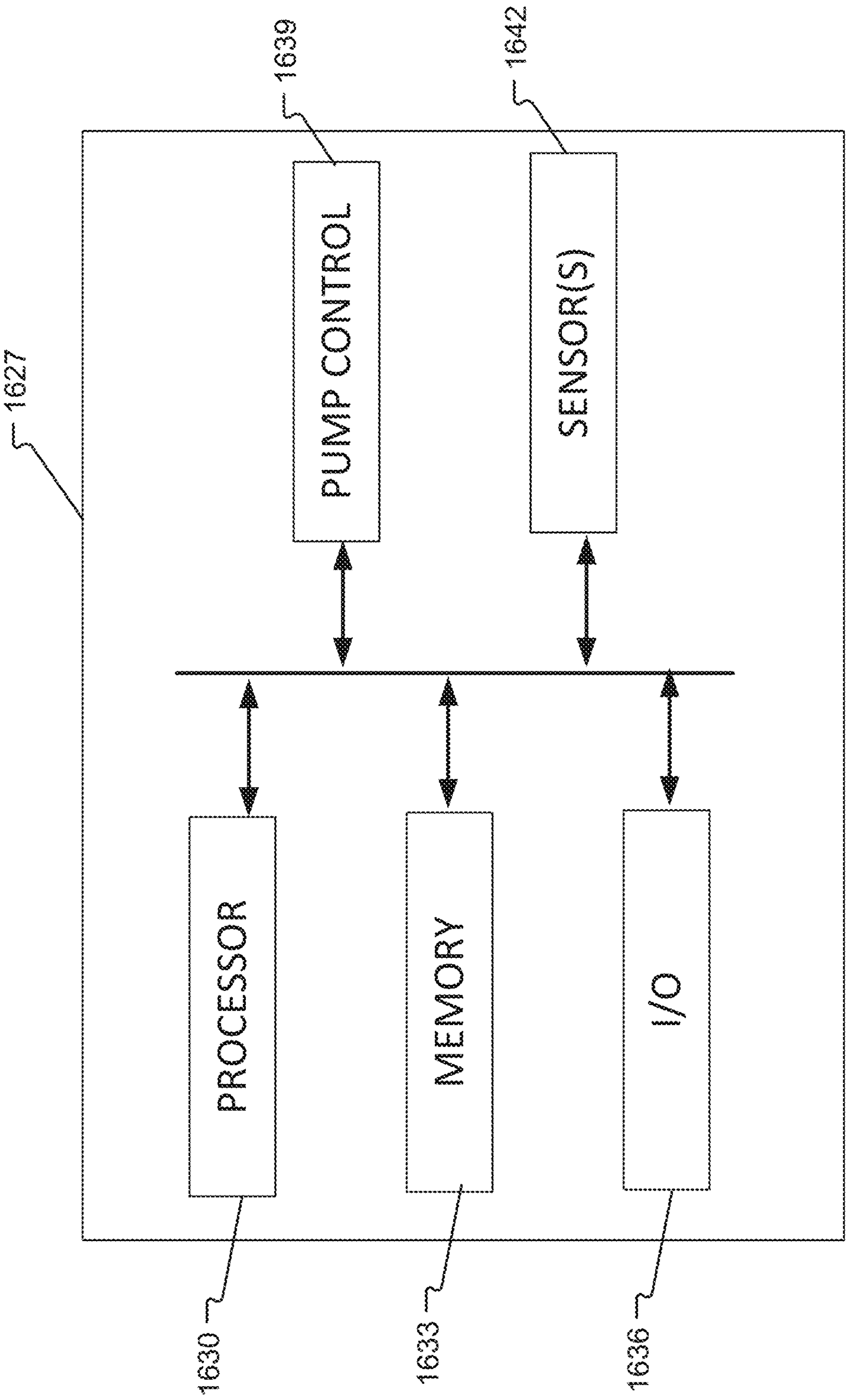
FIG. 10 is a block diagram of an example computing system of the example apheresis system illustrated in FIGS. 1-9 in accordance with at least one example embodiment.
Figure 11:
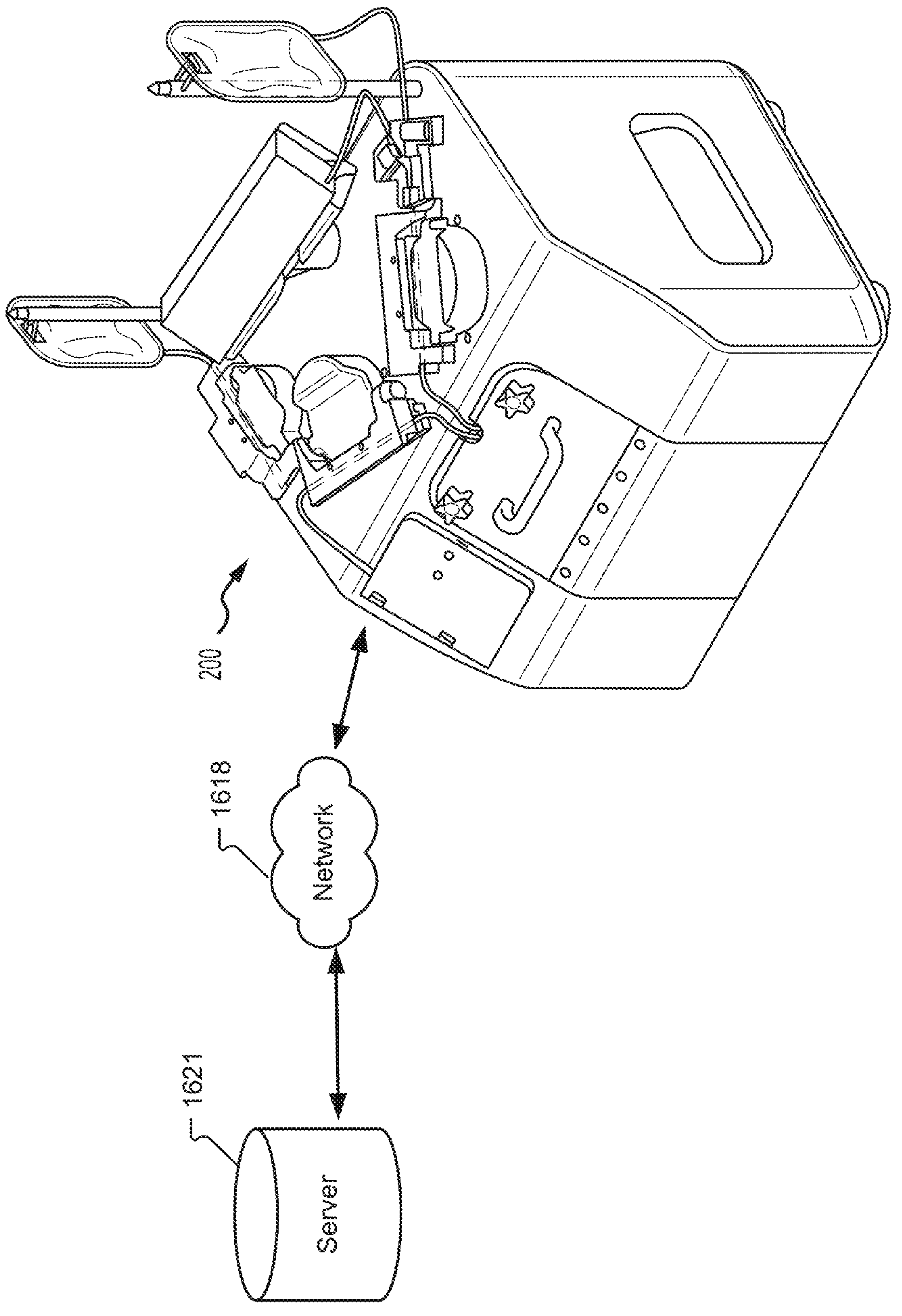
FIG. 11 shows the example apheresis system illustrated in FIGS. 1-10 connected to a network in accordance with at least one example embodiment.

In at least one example embodiment, the apheresis system 200 (for example, via the control system 900 and/or the computer system(s) 1627) may transmit information and/or data to the identification card, or other type of object, and/or to other systems (like a local computer systems), which may be read by other apheresis systems at the same or different donation site. For example, the apheresis system 200 may be configured to send information and/or data, like donation results and/or a current weight of the donor 102 and/or a date and/or time of previous donations and/or various other information. In at least one example embodiment, the apheresis system 200 may include one or more computer systems. For example, as illustrated in FIG. 10, the apheresis system 200 may include one or more computer systems 1627. The computer system(s) 1627 may including, for example, a processor 1630, memory 1633, input/output devices 1636, one or more pump control systems 1639, one or more sensors 1642, and/or other appropriate elements. The processor 1630 may be configured to execute software. The software may include firmware, applications, and/or operating systems which may manage execution of the apheresis system 200. The computer system(s) 1627 may be configured to detect the start 1202 of the apheresis system 200 and/or may be configured to transmit certain information and/or data to a server 1621 via a connection to a network 1618, as illustrated in FIG. 11. In this manner, the apheresis system 200 may communicate certain information and/or data (e.g., a data log, a firmware version identifier, and an error log) with a local system, such as a computer on location at a donation site, which may also be configured to communicate with the server 1621.

Figure 12:
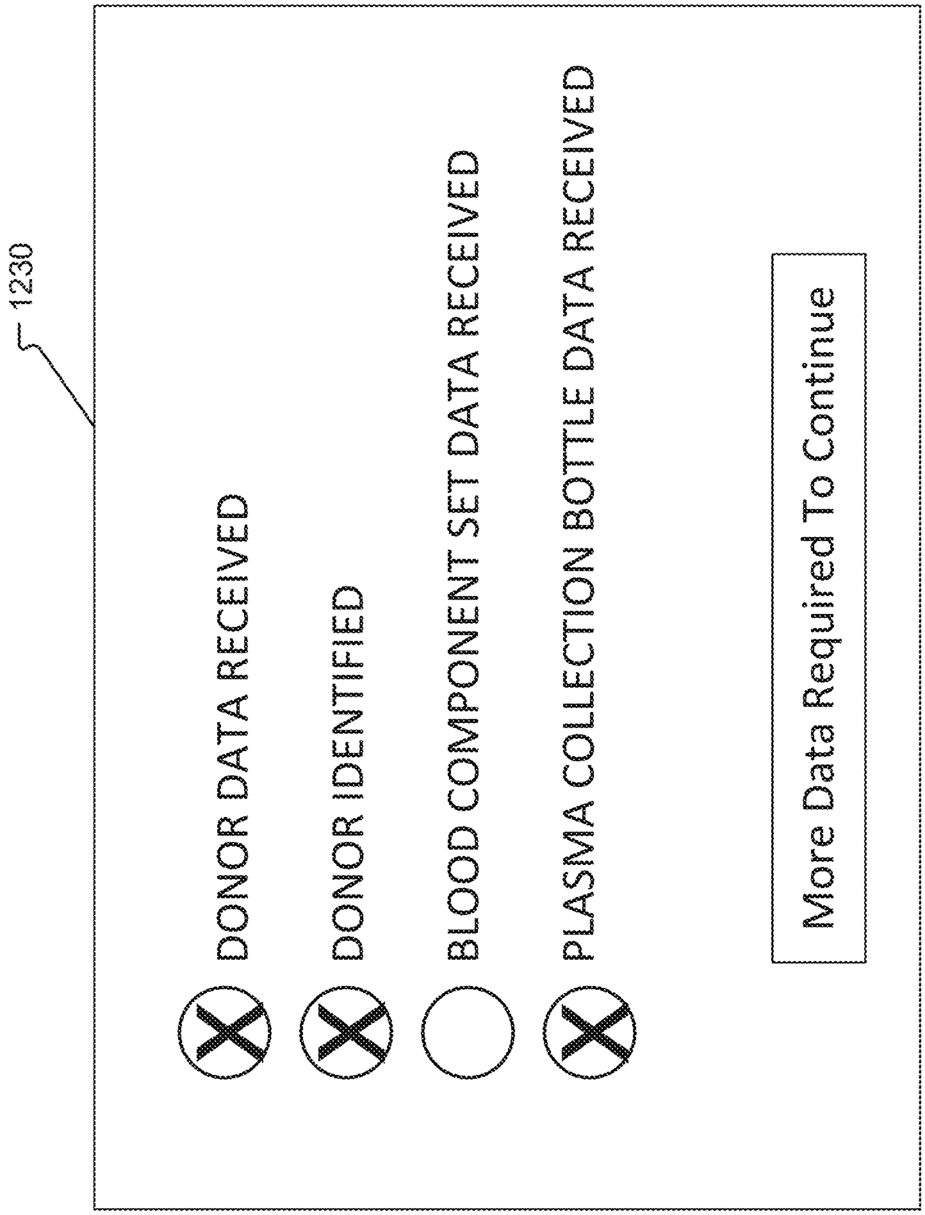
FIG. 12 illustrates an example graphical user interface of the example apheresis system illustrated in FIGS. 1-10 in accordance with at least one example embodiment.

In at least one example embodiment, after receiving the donor specific information and/or data, the apheresis system 200 may be configured to confirm receipt of the information and/data using a feedback system, such as a graphical user interface (GUI) 1230, as illustrated in FIG. 12. In this manner, a nurse, practitioner, or other user or operator of the apheresis system 200 may be able to quickly ascertain whether the donor information and/or data has been properly inputted into the apheresis system 200. In at least one example embodiment, the feedback system may also, or alternatively, include a speaker that may be configured to provide audible feedback.

With renewed reference to FIG. 8, the method 1200 may further include using the received information and/or data to identify 1206 the donor 102. For example, in at least one example embodiment, the apheresis system 200 (for example, using the control system 900 and/or the computer system(s) 1627) may be configured to identify 1206, using the information and/or data received via the scanner 1221, whether the donor 102 is associated with any existing donor 102 identity in a database and/or whether the donor 102 is a new donor.

The method 1200 may also include receiving 1209 information and/or data associated with a blood component collection set to be used during the donation process. In at least one example embodiment, the blood component collection set may include a soft cassette assembly, like the soft cassette assembly 300. In at least one example embodiment, the information and/or data associated with the blood component collection set may be received 1209 by the apheresis system 200 via a barcode, quick release code, radio-frequency identification chip, and/or other type of scannable object that may be associated with the blood component collection set. In at least one example embodiment, each blood component collection set may be affixed with a label or sticker that include a distinct barcode, quick release code, radio-frequency identification chip, and/or other type of scannable object. By scanning the label or sticker on the blood component collection set, the apheresis system 200 may be enabled to record into memory (and in at least one embodiment, shared with the server 1621) which blood component collection set is being used for the current donation process. In this manner, the apheresis system 200 may be enabled to associate donor with a selected blood component collection set. The data associated with the blood component collection set may include, for example, a date of manufacture and/or an identity of manufacturer and/or various other information that may be useful for data processing purposes after the donation is complete. In at least one example embodiment, data associated with the blood component collection set received 1209 through scanning may be used to determine a type of blood component collection set. The type of blood component collection set may be used by the apheresis system 200 to adjust one or more settings such as flow rate or other information during the donation process.

In at least one example embodiment, after scanning the blood component collection set, an operator of the apheresis system 200 may receive confirmation of the receipt of the information from the blood component collection set. For example, a graphical user interface 1230, as illustrated in FIG. 12, may display an indication as to whether data from a blood component collection set has been received. In at least one example embodiment, instead of or in addition to displaying through a graphical user interface 1230, the apheresis system 200 may play an audible sound through one or more speakers or display lights of various colors to indicate the data has been received.

With renewed reference to FIG. 8, in at least one example embodiment, the method 1200 includes receiving 1212 data associated with a collection bottle. For example, in at least one example embodiment, to initialize the apheresis system 200 for a new donor, a collection bottle may be required. After donation, the collection bottle may be filled with the donated plasma (or other fluid). For data tracking purposes, the collection bottle may be required to be associated with the donor making it may be necessary for an identity of the plasma collection bottle to be recorded. As such, an operator of the apheresis system 200 may be enabled to scan a label, sticker, or other object associated with (e.g., printed on or sticked to) the collection bottle using the apheresis system 200. As with the previously detailed steps, upon receiving 1212 the information and/or data from a plasma collection bottle, the apheresis system 200 may acknowledge receipt of the data via a graphical user interface 1230 and/or speaker and/or white, and/or other feedback system.

Figure 13:
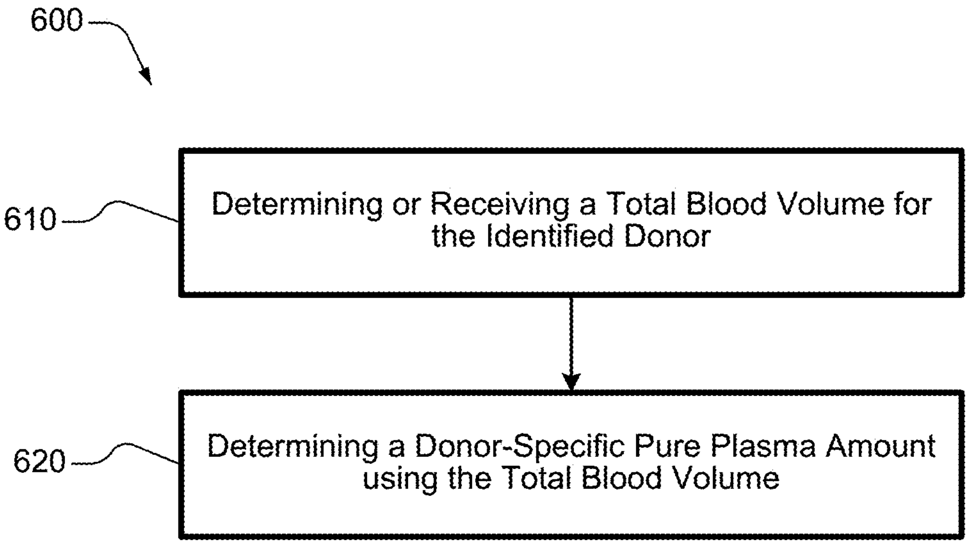
FIG. 13 is a flowchart illustrating an example method for determining a donor-specific pure plasma amount or volume to be collected ("the donated plasma") in accordance with at least one example embodiment.

The method 1200 using the received data and/or information (including the donor-specific information and/or data and/or the blood component collect set information and/or data and/or the collection bottle information and/or data) to determine and/or selected 1213 one or more operating parameters of the plasma donation process. For example, in at least one example embodiment, the apheresis system 200 may be configured (for example, via the control system 900 and/or the computer system(s) 1627) to calculate the amount or volume of plasma (or other component) the donor 102 can provide or donate using the information and/or data received. For example, an example method 600 for determining the amount or volume of plasma the donor 102 can provide or donate is illustrated in FIG. 13.

In at least one example embodiment, the method 600 includes receiving or determining 610 a total blood volume ($TBV_i$) (which may also be referred to an initial total blood volume or the donor's starting total blood volume) for the identified donor 102.

In at least one example embodiment, the total blood volume may be determined using the LEMMENS algorithm, which is copied below:

$$TBV_i = \frac{\text{Weight} \times \text{Ideal}}{\sqrt{\frac{BMI}{22}}} \quad \text{(I)}$$

where the ideal is greater than or equal to about 65 to less than or equal to about 70, and in certain aspects, optionally about 70, weight is the donor's measured weight in kilograms (kg), and the body mass index (BMI) can be determined as follows:

$$BMI = \frac{\text{Weight}}{\text{Height}^2} \quad \text{(II)}$$

where height is the donor's measured height in meters (m).

In other example embodiments, the total blood volume may be determined using the NADLER algorithm, which is copied below:

$$TBV_m = (0.3669 \times \text{Height}^3) + (0.03219 \times \text{Weight}) + 0.6041 \quad \text{(III)}$$

$$TBV_f = (0.3561 \times \text{Height}^3) + (0.03308 \times \text{Weight}) + 0.1833 \quad \text{(IV)}$$

where $TBV_m$ is the algorithm for persons assigned male at birth and $TBV_f$ is the algorithm for persons assigned female at birth.

The weight is a measured weight for the donor 102. The height is a measured height for the donor 102. In at least one example embodiment, the weight and/or height and/or body mass index may be communicated to the apheresis system 200 (and more specifically the control system 900 and/or the computer system(s) 1627) via the donor identification card, or other type of object, as discussed above, and/or from inputs made by an operator, for example, via the graphical user interface 1230. The apheresis system 200 (and more specifically the control system 900 and/or the computer system(s) 1627) may be configured to determine the body mass index and/or to receive a pre-determined body mass index, for example, from the donor identification card, or other type of object, and/or from inputs made by a nurse, practitioner, or other user or operator of the apheresis system 200, for example, via the graphical user interface 1230. The apheresis system 200 (and more specifically the control system 900 and/or the computer system(s) 1627) may be configured to determine the total blood volume ($TBV_i$) using, for example, the LEMMENS algorithm and/or the NADLER algorithm, and/or to receive a pre-determined the total blood volume, for example, from the donor identification card, or other type of object, and/or from inputs made by a nurse, practitioner, or other user or operator of the apheresis system 200, for example, via the graphical user interface 1230.

With renewed reference to FIG. 13, the method 600 may include determining 620 a donor-specific component amount. Determining 620 a donor-specific component amount may include using one or more of the below noted relationships.

As illustrated below, the total blood volume ($TBV_i$) is equal to the sum of a final total blood volume ($TBV_f$) (which is the total blood volume for the donor after donation) and a donated platelet amount (which is a volume of the donated pure platelets in plasma) and a donated plasma amount (which is a volume of the donated pure plasma) and a donated red blood cell amount (which is a volume of the donated blood cells at 100% hematocrit) divided by a hematocrit of the donated red blood cells ($hct_{dr}$) (which is typically about 80%).

$$TBV_i = TBV_f + \text{donated platelets} + \text{donated plasma} + \frac{\text{donated } rbcs}{hct_{dr}} \quad \text{(V)}$$

As illustrated below, a product of the total blood volume ($TBV_i$) and a donor's initial hematocrit ($hct_i$) equals the sum of a product of the final total blood volume ($TBV_f$) and a donor's final hematocrit ($hct_f$) and the donated red blood cell amount.

$$TBV_i * hct_i = (TBV_f * hct_f) + \text{donated } rbcs \quad \text{(VI)}$$

Relationships (V) and (VI) as introduced may be combined to solve for various component amounts.

In at least one example embodiment, a pure plasma amount or volume to be collected may be determined at 620. The donor-specific pure plasma (i.e., platelets and red blood cells=0) amount or volume to be collected ("the donated plasma") may be determined using the as-determined or as-received total blood volume ($TBV_i$) and/or an initial hematocrit ($hct_i$) and/or and a targeted change in hematocrit, for example, in accordance with the following relationships.

$$TBV_i * hct_i = (TBV_f * hct_f) \quad \text{(VII)}$$

-continued $$TBV_i * hct_i = A * B \tag{VIII}$$

$$A = (TBV_f - \text{donated plasma}) \tag{XI}$$

$$B = (hct_i + \text{Targeted Change in Hematocrit}) \tag{X}$$

$$\text{donated plasma} = TBV_i - \frac{TBV_i \times hct_i}{hct_i + \text{Targeted Change in Hematocrit}} \tag{XI}$$

For example, by way of example only, a donor having a total blood volume of 4,000 mL, a hematocrit ($hct_i$) of 0.45, and a targeted change in hematocrit of 8%, the amount of donated plasma to be collected may be determined as follows:

$$\text{donated plasma} = 4000 - \frac{4000 \times 0.45}{0.45 + 0.08} = 604 \text{ mL} \tag{XII}$$

The hematocrit ($hct_i$) is a measured hematocrit (i.e., volume fraction of red blood cells in the blood, in decimal form) for the donor 102 and may be communicated to the apheresis system 200 (and more specifically the control system 900 and/or the computer system(s) 1627) via the donor identification card, or other type of object, as discussed above, and/or from inputs made by a nurse, practitioner, or other user or operator of the apheresis system 200, for example, via the graphical user interface 1230. The apheresis system 200 (and more specifically the control system 900 and/or the computer system(s) 1627) may be configured to perform plasma donation 1215 and/or determine 620 the donor-specific pure plasma amount or volume to be collected only if the hematocrit is found to be within a predetermined threshold, for example, between greater than or equal to about 0.38 to less than or equal to about 0.54.

Hematocrit levels increase as plasma is removed from the donor. The targeted change in hematocrit reflects this difference and is selected as a desired constant. The targeted change in hematocrit is a fixed, donor-generic value that may be received and/or generated by and/or stored locally by the apheresis system 200 (and more specifically the control system 900 and/or the computer system(s) 1627). In at least one example embodiment, the targeted change in hematocrit may be communicated to the apheresis system 200 (and more specifically the control system 900 and/or the computer system(s) 1627) via the server 1621.

The targeted change in hematocrit is selected so the donor's post-hematocrit is an acceptable, safe post-hematocrit, for example, as determined by different regulatory authorities. In at least one example embodiment, the targeted change in hematocrit may be greater than or equal to about 1% (e.g., greater than or equal to about 1.5%, greater than or equal to about 2%, greater than or equal to about 2.5%, greater than or equal to about 3%, greater than or equal to about 3.5%, greater than or equal to about 4%, greater than or equal to about 4.5%, greater than or equal to about 5%, greater than or equal to about 5.5%, greater than or equal to about 6%, greater than or equal to about 6.5%, greater than or equal to about 7%, greater than or equal to about 7.5%, greater than or equal to about 8%, greater than or equal to about 8.5%, greater than or equal to about 9%, greater than or equal to about 9.5%, greater than or equal to about 10%, greater than or equal to about 10.5%, greater than or equal to about 11%, greater than or equal to about 11.5%, greater than or equal to about 12%, greater than or equal to about 12.5%, greater than or equal to about 13%, greater than or equal to about 13.5%, greater than or equal to about 14%, greater than or equal to about 14.5%). In at least one example embodiment, the targeted change in hematocrit may be less than or equal to about 15% (e.g., less than or equal to about 14.5%, less than or equal to about 14%, less than or equal to about 13.5%, less than or equal to about 13%, less than or equal to about 12.5%, less than or equal to about 12%, less than or equal to about 11.5%, less than or equal to about 11%, less than or equal to about 10.5%, less than or equal to about 10%, less than or equal to about 9.5%, less than or equal to about 9%, less than or equal to about 8.5%, less than or equal to about 8%, less than or equal to about 7.5%, less than or equal to about 7%, less than or equal to about 6.5%, less than or equal to about 6%, less than or equal to about 5.5%, less than or equal to about 5%, less than or equal to about 4.5%, less than or equal to about 4%, less than or equal to about 3.5%, less than or equal to about 3%, less than or equal to about 2.5%, less than or equal to about 2%, less than or equal to about 1.5%). In at least one example embodiment, the targeted change in hematocrit may range from about 1% to about 15% (e.g., from about 2% to about 14%, from about 3% to about 13%, from about 4% to about 12%, from about 5% to about 11%, from about 6% to about 10%, from about 7% to about 9%). In at least one example embodiment, the targeted change in hematocrit may be about 8%.

In at least one example embodiment, a pure red blood cell (i.e., platelets and plasma=0) amount or volume to be collected ("the donated red blood cell") may be determined at 620. The donor-specific red blood cell amount or volume to be collected may be determined using the as-determined or as-received total blood volume ($TBV_i$) and/or an initial hematocrit ($hct_i$), for example, in accordance with the following relationships.

$$TBV_f = TBV_i - \frac{\text{donated } rbcs}{hct_{dr}} \tag{XIII}$$

$$\text{donated } rbcs = TBV_i * hct_i - TBV_f * hct_f \tag{XIV}$$

$$\text{donated } rbcs = TBV_i * hct_i - TBV_i * hct_f + \left(\frac{\text{donated } rbcs}{hct_{dr}}\right) * hct_f \tag{XV}$$

$$\text{donated } rbcs - \left(\frac{\text{donated } rbcs}{hct_{dr}}\right) * hct_f = TBV_i * hct_i - TBV_i * hct_f \tag{XVI}$$

$$\left(\frac{\text{donated } rbcs}{hct_f}\right) - \left(\frac{\text{donated } rbcs}{hct_{dr}}\right) = \left(\frac{TBV_i * hct_i}{hct_f}\right) - TBV_i \tag{XVII}$$

$$\text{donated } rbcs - \left(\frac{1}{hct_f} - \frac{1}{hct_{dr}}\right) = TBV_i * \left(\frac{hct_i}{hct_f} - 1\right) \tag{XVIII}$$

$$\text{donated } rbcs = \frac{\left(TBV_i * \left(\frac{hct_i}{hct_f} - 1\right)\right)}{\left(\frac{1}{hct_f} - \frac{1}{hct_{dr}}\right)} \tag{XIX}$$

With renewed reference to FIG. 8, the method 1200 may end at 1218, at which point the donation process may continue with the extraction of fluids from the donor being completed. Any information and/or data received through the above discussed steps may be recorded into memory and/or shared with one or more computer systems 1627. For example, a database entry may be created for the particular donation, including information such as an amount or volume of plasma extracted from the donor, a current weight of the donor, a time and/or date of the donation, and/or other information and/or data.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method for collection of blood component using a medical system, the method comprising:

receiving, by the medical system, data associated with an individual subject, the data associated with the individual subject including a subject's initial hematocrit;

identifying, by the medical system, a subject-specific pure component amount to be collected by the medical system, the subject-specific pure component amount to be collected by the medical system determined using the subject's initial hematocrit, an initial total blood volume for the subject, and a targeted change in hematocrit, the subject-specific pure component amount including plasma and determined by, the medical system, in accordance with the following relationship:

$$\text{pure plasma} = TBV_i - \frac{TBV_i \times hct_i}{hct_i + \text{Targeted Change in Hematocrit}}$$

where $TBV_i$ is the initial total blood volume for the subject and $hct_i$ is the subject's initial hematocrit; and performing, using the medical system, a component donation process to collect the identified subject-specific pure component amount to be collected.

2. The method of claim 1, wherein the receiving of the data associated with the individual subject includes scanning, with a scanner, an image.

3. The method of claim 2, wherein the scanner is disposed on the medical system.

4. The method of claim 2, wherein the image includes a one-dimensional barcode, a two-dimensional barcode, or a combination of a one-dimensional barcode and a two-dimensional barcode.

5. The method of claim 1, further including:

determining, by the medical system, using the received data associated with an individual subject, an identification of the subject; and adjusting, by the medical system, one or more parameters of the component donation process.

6. The method of claim 1, further including:

receiving, by the medical system, data associated with a blood component collection set; and adjusting, by the medical systems, one or more parameters of the component donation process.

7. The method of claim 1, further including:

receiving, by the medical system, data associated with a component collection bottle; and adjusting, by the medical systems, one or more parameters of the component donation process.

8. The method of claim 1, wherein the data associated with the individual subject further includes the total blood volume.

9. The method of claim 1, further including:

determining, by the medical system, using the received data associated with an individual subject, the total blood volume for the subject.

10. The method of claim 9, further including:

determining, by the medical system, using the received data associated with an individual subject, a body mass index of the subject.

11. The method of claim 1, wherein the targeted change in hematocrit is a preselected constant ranging from about 1% to about 15%.

12. The method of claim 1, wherein the targeted change in hematocrit is selected based on the subject's initial hematocrit and an acceptable post-hematocrit level.

13. The method of claim 12, wherein a difference between the subject's initial hematocrit and the acceptable post-hematocrit level ranges from about 1% to about 15%.

14. The method of claim 11, wherein the targeted change in hematocrit is about 8%.

15. The method of claim 1, further including:

after receiving the data associated with the individual subject, confirming receipt of the same using a feedback system.

16. The method of claim 15, wherein the feedback system includes a speaker, a graphical user interface, or a speaker in combination with a graphical user interface.

* * * * *